US009770021B2

(12) United States Patent
Keiper et al.

(10) Patent No.: US 9,770,021 B2
(45) Date of Patent: Sep. 26, 2017

(54) PESTICIDAL COMPOSITIONS

(75) Inventors: Jason Keiper, Greensboro, NC (US); Joshua Koon, Greensboro, NC (US); Sarah Beth Cush, Greensboro, NC (US); Michael James Hopkinson, Greensboro, NC (US); Johnny D. Reynolds, Greensboro, NC (US); Jorge Cisneros, Basel (CH); Jennifer Peterson, Greensboro, NC (US); Roy Boykin, Greensboro, NC (US)

(73) Assignee: Syngenta Participations AG, Basel (CH)

( * ) Notice: Subject to any disclaimer, the term of this patent is extended or adjusted under 35 U.S.C. 154(b) by 282 days.

(21) Appl. No.: 12/993,758

(22) PCT Filed: May 25, 2009

(86) PCT No.: PCT/EP2009/056294
§ 371 (c)(1),
(2), (4) Date: Apr. 18, 2011

(87) PCT Pub. No.: WO2009/138523
PCT Pub. Date: Nov. 19, 2009

(65) Prior Publication Data
US 2011/0189294 A1 Aug. 4, 2011

Related U.S. Application Data

(60) Provisional application No. 61/052,358, filed on May 12, 2008.

(51) Int. Cl.
| | | |
|---|---|---|
| A01N 53/06 | (2006.01) | |
| A01N 43/56 | (2006.01) | |
| A01N 43/36 | (2006.01) | |
| A01N 31/14 | (2006.01) | |
| A01N 37/18 | (2006.01) | |
| A01N 43/54 | (2006.01) | |
| A01N 35/10 | (2006.01) | |
| A01N 43/40 | (2006.01) | |
| A01N 43/88 | (2006.01) | |
| A01N 25/12 | (2006.01) | |
| A01N 43/38 | (2006.01) | |
| A01N 53/02 | (2006.01) | |
| A01N 25/30 | (2006.01) | |
| A01N 25/04 | (2006.01) | |
| A01N 43/90 | (2006.01) | |

(52) U.S. Cl.
CPC ............. *A01N 25/30* (2013.01); *A01N 25/04* (2013.01); *A01N 43/90* (2013.01)

(58) Field of Classification Search
None
See application file for complete search history.

(56) References Cited

U.S. PATENT DOCUMENTS

| | | |
|---|---|---|
| 5,128,329 A | 7/1992 | Minagawa et al. |
| 5,393,770 A | 2/1995 | Grayson |
| 6,096,769 A | 8/2000 | Perlitz et al. |
| 2005/0043182 A1 | 2/2005 | Douglass et al. |
| 2007/0179058 A1 | 8/2007 | Baum |
| 2007/0196358 A1 | 8/2007 | Haulsee et al. |
| 2007/0225169 A1 | 9/2007 | Hopkinson et al. |
| 2008/0214632 A1* | 9/2008 | Hamel .................. A01N 43/90 514/370 |
| 2009/0137667 A1* | 5/2009 | Kabanov et al. ............. 514/531 |
| 2011/0189294 A1 | 8/2011 | Keiper et al. |

FOREIGN PATENT DOCUMENTS

| | | | |
|---|---|---|---|
| CN | 1063914 A | 8/1991 | |
| CN | 1781372 A | 12/2004 | |
| CN | 1925746 A | 3/2007 | |
| CN | 101002559 A | 7/2007 | |
| DE | WO 2005089550 A2 * | 9/2005 | ............. A01N 43/90 |
| EP | 0388239 A1 | 3/1990 | |
| EP | 1204316 B1 | 11/2004 | |
| JP | H06316502 A | 11/1994 | |
| WO | 02/03798 A1 | 1/2002 | |
| WO | 0203798 | 1/2002 | |

(Continued)

OTHER PUBLICATIONS

"The HLB System a time-saving guide to emulsifier selection" ICI Americas Inc. (1976).*
Opposition of European Patent No. 2303007 filed by BASF SE on Nov. 16, 2016.
Griffin, Wiliam C., "Calculation of HLB Values of Non-Ionic Surfactants", Journal of the Society of Cosmetic Chemists, May 14, 1954 meeting, NYC, Atlas Powder Company, Wilmington, Delaware, pp. 249-256.
Davies, J.T., "A Quantitative Kinetic Theory of Emulsion Type. I. Physical Chemistry of the Emulsifying Agent", Reprinted from: Gas/Liquid and Liquid/Liquid Interfaces. Proceedings of 2nd International Congress Surface Activity, Butterworths, London 1957.
The Pesticide Manual, British Crop Protection Council, Fourteenth Edition, 2006, p. 677.

(Continued)

*Primary Examiner* — John Pak
*Assistant Examiner* — Daniel Branson
(74) *Attorney, Agent, or Firm* — James Cueva

(57) ABSTRACT

A formulated composition suitable for controlling or preventing pathogenic damage in a plant comprising (A) at least one solid active ingredient having a water solubility of at most 100 μg/liter at 25° C. at neutral pH, in an amount of at least 1 weight %, based on the total weight of the formulated composition, (B) at least one non-ionic surface active compound having a hydrophile-lipophile balance (HLB) of between 10 and 18, one or more customary formulation auxiliaries, and water; wherein active ingredient (A) is suspended or dispersed in the water, the weight ratio of surface active compound (B) to active ingredient (A) is in the range of from 1.5 to 15.0, provided the minimum amount of surface active compound (B) is at least 6 weight %, based on the total weight of the formulated composition. Also a method of improving pesticide residue levels in agriculture.

11 Claims, No Drawings

(56) References Cited

FOREIGN PATENT DOCUMENTS

| WO | 02/19821 A1 | 3/2002 |
|---|---|---|
| WO | 03/022049 A1 | 3/2003 |
| WO | 2005/048707 A1 | 6/2005 |
| WO | 2005089546 A1 | 9/2005 |
| WO | WO 2005089546 A1 * | 9/2005 |
| WO | 2006069580 | 7/2006 |
| WO | 2006069580 A1 | 7/2006 |
| WO | 2007/003319 A2 | 1/2007 |
| WO | 2007/081961 A2 | 7/2007 |
| WO | 2007/112834 A2 | 10/2007 |
| WO | 2008/040727 A2 | 4/2008 |
| WO | 2009/138523 A3 | 11/2009 |

OTHER PUBLICATIONS

Technical Bulletin, Pluronic P105, Block Copolymer Surfactant, BASF, 2004.
The Pesticide Manual, British Crop Protection Council, Fourteenth Edition, 2006, pp. 938-939.
The HLB System: a time-saving guide to emulsifier selection, ICI Americas Inc., Mar. 1980.
The Pesticide Manual, British Crop Protection Council, Fourteenth Edition, 2006, p. 513.
The Pesticide Manual, British Crop Protection Council, Fourteenth Edition, 2006, pp. 484-485.
Technical Information Pluronic PE types, BASF, Nov. 2002.
Alexandridis, P. et al., Poly(ethylene oxide)-poly(propylene oxide)-poly(ethylene oxide) block copolymer surfactants in aqueous solutions and at interfaces: thermodynamics, structure, dynamics and modeling Colloids and Surfaces A: Physicochemical and Engineering Aspects; 96 (1995) pp. 1-46.
The Pesticide Manual, British Crop Protection Council, Fourteenth Edition, 2006, pp. 32-33.
Momentive, Silwet Copolymers Chameleon Solutions, technical brochure, 2004.
Functional Products, Agnique PG 8107-U, Cognis Corporation, literature, (Sep. 3, 2009).
"Introduction to Cognis Additives, Inerts, Solvents and Adjuvants for Agrochemicals", Cognis tecnial brochure, 2007.
The Pesticide Manual, British Crop Protection Council, Fourteenth Edition, 2006, pp. 94-95.
Neodol Ethoxylates, Properties and Comparison Guide, Shell Chemical Company, Oct. 1997.
ThePesticide Manual, British Crop Protection Council, Fourteenth Edition, 2006, pp. 421-422.
BASF Safety Data Sheet, Product: Alverde, Mar. 19, 2008.
Knowles, A., "Trends in Pesticide Formulations", Suspension Concentrates, Chapter 7, (2007), pp. 37-40.
The Pesticide Manual, British Crop Protection Council, Fourteenth Edition, 2006, p. 331.
Response to Opposition of European Patent No. EP 23030071 filed May 2, 2017.
Aulton, M.E., Pharmaceutics, The Science of Dosage Form Design, 2ed., pp. 95-99.

* cited by examiner

PESTICIDAL COMPOSITIONS

This application is a 371 of International Application No. PCT/EP2009/056294 filed May 25, 2009, which claims priority to U.S. 61/052358 filed May 12, 2008, the contents of which are incorporated herein by reference.

The present invention relates to a formulated composition comprising a certain active ingredient either suspended or dispersed in water and a defined amount of a defined surface active compound, a tank-mix composition thereof, and their use for combating pests. The present invention also relates to a composition demonstrating improved pesticide residue levels.

The efficient use of pesticides is often restricted somewhat by their inherent poor water-solubility. Generally, these water-insoluble pesticides can be applied to a site in three ways: 1) as a dust, 2) as a solution in an organic solvent or a combination of water and one or more organic solvents, or 3) as an emulsion that is prepared by dissolving the product in an organic solvent, then dispersing the solution in water. All of these approaches have drawbacks:
- application of a dust poses a health hazard and is inefficient.
- solutions and emulsions requiring an organic solvent as the main carrier are undesirable since the solvent usually serves no other purpose but to act as a carrier for the product and as such, the solvent adds an unnecessary cost to the formulation, and the solvent itself can be environmentally harmful.

Another drawback is the efficacy/stability issues associated with a water-based formulations, such as suspension concentrates and suspo emulsions. On such example of a drawback is that water-based formulations containing solid active ingredients or formulation aids may exhibit settling of the suspended or dispersed components over time. This settling can lead to the creation of hard packed sediment making it difficult to get the materials out of the container. In many cases, the pesticide solids pesticides may stay suspended in the formulated concentrate but upon dilution of these types of formulations, the suspended or dispersed solids will settle with time to the bottom of a container. The rate of sedimentation depends on a number of factors such as particle size, particle concentration, viscosity of the suspending medium and the specific gravity difference between the particles and the suspending medium. Once settled, the sediments may become hard packed in nature, making redispersion or resuspension extremely difficult. The creation of hard packed sediment can occur when the tanks are not agitated. Interruptions in the spray schedule frequently occur due to normal breaks, for example overnight, taken by the applicator, weather changes, mechanical malfunction or unforeseen events which result in non-agitation of the spray tank.

It would be an advantage in the art, therefore, to provide a pesticide formulation that eliminates the need for organic solvents as a carrier, on the one hand, but exhibits optimal availability to the site to which it is applied.

The efficacy of the active components can often be improved by addition of other ingredients such as adjuvants. An adjuvant is defined here as a substance which can increase the biological activity of an active ingredient but is not itself significantly biologically active.

Generally, an adjuvant is added to the spray tank together with the formulation containing the active ingredient. Further, in view of an easy and safe handling and dosing of these adjuvants by the end-user and in view of avoiding unnecessary packing material, it is desirable to develop concentrated formulations which already contain such adjuvants.

However, arriving at a formulation demonstrating physicochemical stability and biological efficacy is a challenge to a skilled person.

The present inventors have found that certain surface active compounds, when used in a defined amount and a defined ratio with a low water soluble active ingredient in a formulation offers benefits hereto before not met with water-based formulations.

Accordingly, in a first aspect the present invention provides a formulated composition, preferably an agrochemical formulated composition, comprising (A) at least one solid active ingredient having a water solubility of at most 100 µg/litre at 25° C. at neutral pH, in an amount of at least 1 weight %, based on the total weight of the formulated composition, (B) at least one non-ionic surface active compound having a hydrophile-lipophile balance (HLB) of between 10 and 18, one or more customary formulation auxiliaries, and water
wherein active ingredient (A) is suspended or dispersed in the water, the weight ratio of surface active compound (B) to active ingredient (A) is in the range of from 1.5 to 15.0, provided the minimum amount of surface active compound (B) is at least 6 weight %, based on the total weight of the formulated composition.

The formulated composition of the first aspect demonstrates improved translaminarity and re-suspension characteristics compared to a similarly formulated composition which does not comprise said surface—active compound defined in the first aspect.

Therefore, in a second aspect the present invention provides a method of improving the translaminarity of an active ingredient (A), as defined the first aspect, comprising forming a formulated composition comprising at least one non-ionic surface active compound having a hydrophile-lipophile balance (HLB) of between 10 and 18 (compound (B)), wherein the weight ratio of surface active compound (B) to active ingredient (A) is in the range of from 1.5 to 15.0, provided the minimum amount of surface active compound (B) is at least 6 weight %, based on the total weight of the formulated composition.

In a third aspect, the present invention provides a method for improving the re-suspension properties of a suspension comprising forming a composition comprising at least one solid active ingredient (A), as defined in the first aspect, and at least one non-ionic surface active compound having a hydrophile-lipophile balance (HLB) of between 10 and 18 (compound (B)), wherein the weight ratio of surface active compound (B) to active ingredient (A) is in the range of from 1.5 to 15.0, provided the minimum amount of surface active compound (B) is at least 6 weight %, based on the total weight of the composition.

The formulated compositions of the present invention at effective amounts can be not phytotoxic, show rainfastness and demonstrate improved UV stability, and thereby exhibit optimal availability to the site to which it is applied. Indeed, it has been found that the formulated composition of the first aspect offers acceptable physical, chemical and biological characteristics.

Accordingly, in a fourth aspect, the present invention provides a method of controlling or preventing pathogenic damage or pest damage in a plant propagation material, a plant, parts of a plant and/or plant organs that grow at a later point in time, which comprises applying on the plant, part of the plant, plant organs, plant propagation material or a surrounding area thereof a composition derived from the formulated composition defined in the first aspect.

A pesticide is a substance or mixture of substances used to kill a pest. A pesticide may be a chemical substance (such as an active ingredient), biological agent (such as a virus or bacteria), antimicrobial, disinfectant or device used against any pest. Pests include insects, plant pathogens, weeds, molluscs, birds, mammals, fish, nematodes (roundworms) and microbes that compete with humans for food, destroy property, spread or are a vector for disease or cause a nuisance. Although there are benefits to the use of pesticides, there are also drawbacks, such as potential toxicity to humans and other animals. Therefore, pesticide residue refers to the pesticides that may remain on or in food after they are applied to food crops. An authority in a country, such as the Environmental Protection Agency (EPA) in USA, sets limits on how much of a pesticide residue can remain on food and feed products, or commodities. These pesticide residue limits are known as tolerances (they are referred to as maximum residue limits, or MRLs, in many other countries). Tolerances are set to protect consumers from harmful levels of pesticides on food. Accordingly, EPA is responsible for regulating the pesticides that are used by growers to protect crops and for setting pesticide residue in USA.

Active ingredients mentioned herein are deemed pesticides, such as active ingredient (A) and active ingredient (D).

It has been found that use of one or more adjuvants with an aqueous formulated composition comprising a pesticide, especially abamectin, reduces the pesticide residue levels on a plant. The adjuvants referred to herein are those commonly used in the agriculture, of which a skilled person would know. However, the present invention especially concerns adjuvants having non-ionic surfactants and/or oil components, and are commonly known as non-ionic adjuvants. An adjuvant generally tends to be a mixture or blend of components.

Accordingly, in a further aspect the invention provides a method of improving (or decreasing) the pesticide residue on a plant comprising applying a tank-mix composition comprising (I) a pesticidal composition which comprises a pesticide defined in the first aspect, such as abamectin, a solvent, such as water, and (II) one or more adjuvants, to the plant, part of the plant, plant organs, plant propagation material, wherein the adjuvant is present in an amount of from 0.05 to 0.5% by volume, based on the volume of the tank-mix composition, and the adjuvant has one or more non-ionic surfactants and/or oil components.

In an embodiment, the amount of adjuvant is 0.06 to 0.3, preferably 0.075 to 0.25, such as 0.08 to 0.15, % by volume based on volume of the tank-mix composition.

In an embodiment, the tank-mix composition further comprises (III) one or more other pesticide formulated compositions The adjuvants tend to contain a mixture or blend of components, such as alcohols, oil components and/or non-ionic surfactants, including emulsifiers, with the oil components and/or non-ionic surfactants forming a major proportion of the adjuvant.

Examples of oil components in an adjuvant include paraffin oil, horticultural spray oils (e.g., summer oil), methylated rape seed oil, highly refined vegetable oil, etc.

Examples of non-ionic surfactants include polyol fatty acid esters, polyethoxylated esters thereof, ethoxylated alcohols, alkyl polysaccharides & blends, amine ethoxylates, sorbitan fatty acid ester ethoxylates, PEG esters, organosilicone based surfactants, ethylene vinyl acetate terpolymers, and ethoxylated alkyl aryl phosphate esters.

In an embodiment, it has been found that one or more adjuvants decrease the UV stability of a pesticide, especially abamectin, i.e, the UV degradation of the pesticide is improved. Further, the reduced particle size of the pesticide also contributes to the degradation.

The invention is described in more detail below.

Examples of formulation types include granules
wettable powders
water dispersable granules (powders)
water soluble granules
soluble concentrates
emulsifiable concentrate
emulsions, oil in water
micro-emulsion
aqueous suspension concentrate
aqueous capsule suspension
oil-based suspension concentrate, and
aqueous suspo-emulsion.

A formulation is referred to as a concentrate when the concentration of the active ingredient is such that dilution of the formulation (e.g. with water, solvent) is required before it use (for example, on a plant, seed or locus thereof). Generally, the end user will dilute the concentrate to arrive at a spray tank composition (or mixture) or a tank-mix before using it. Other formulated pesticidal ingredients and other adjuvants may be included in the spray tank-composition. Alternatively, depending on the concentration of the active ingredient in the formulation and use of the formulation, the end-user could use the formulation directly, if necessary in combination with other formulation(s), preferably other pesticidal formulation(s). It would, therefore, be clear to a skilled person that a formulated composition as defined in the first aspect corresponds to a formulation, whether as a concentrate for dilution before use or use without dilution. In an embodiment, the present invention relates to a concentrated formulation.

The present invention is directed to water-based formulations. In particular, formulations where the solid active ingredient defined in the first aspect is either suspended or dispersed in water. Examples of such formulations include suspension concentrates and suspoemulsions. The active ingredient can be of any type, or a mixture of different types, preferably at least one active ingredient in the formulation exhibits nematicide and/or insecticide efficacy. The formulated composition may therefore contain organic solvents (such as anti-freeze, etc,) but not to affect the active ingredient (A)'s suspension or dispersion in water. Accordingly, a typical volatile organic content (VOC) level for a formulated composition according to the first aspect is less than 30, preferably less than 20, especially in the range of 5 to 15, %.

In the instance the formulated composition comprises one or more further active ingredient (D) in combination with active ingredient (A), the or each active ingredient (A) is suspended or dispersed in an aqueous phase and the or each active ingredient (D), independently of each other, may be also or dispersed in the aqueous phase or be provided in an encapsulated form (e.g. as a microcapsule).

Solid active ingredients include those solid components that remain dispersed or suspended in the formulation, including the diluted composition. Although the pesticidally active ingredients may exhibit some solubility in the carrier, preferably water, typically the pesticidally active ingredients will be substantially insoluble in the selected carrier, such as water. These substantially water insoluble pesticidally active ingredients may sometimes be referred to herein for brevity as a "water-insoluble" active ingredients even if they have measurable solubility in the selected carrier. It will be apparent to one skilled in the art that the solubility in water of some active ingredients depends on pH if they have a titratable acid or base functionality; specifically acids are more soluble above their pKa and bases are more soluble below their pKb. Thus acids may be rendered insoluble in water for the purposes of the present discussion if the aqueous phase is maintained at a pH close to or below their pKa, even if they may be more soluble than about 5000 mg/l at a higher pH.

Specific examples of the active ingredient (A) include abamectin, acrinathrin, alpha-cypermethrin, acequinocyl, amitraz, benomyl, beta-cyfluthrin, bifenthrin, bioresmethrin, bistrifluron, bromopropylate, chlorethoxyfos, chlorfluazuron, clofentezine, cyfluthrin, cyhalothrin, cypermethrin, cyphenothrin, dodemorph, esfenvalerate, etofenprox, fenvalerate, flucycloxuron, flufenoxuron, hydramethylnon, lambda-cyhalothrin, lufenuron, mecarbam, novaluron, permethrin, phenothrin, silafluofen, tau-fluvalinate, ZXI 8901 (3-(4-bromophenoxy)-a-cyanobenzyl 2-[4-(difluoromethoxy)phenyl]-3-methylbutanoate), and flubendiamide (3-iodo-N'-(2-mesyl-1,1-dimethylethyl)-N-{4-[1,2,2,2-tetrafluoro-1-(trifluoromethyl)ethyl]o-tolyl}phthalamide).

In an embodiment of each aspect of the present invention, at least one active ingredient (A) is selected from abamectin, and lufenuron; preferably active ingredient (A) is abamectin.

Surfactants generally tend to have a HLB of between 4 to 27 and are of different types. It is has been found that non-ionic surface active compounds with a defined HLB have advantageous properties when used in defined amounts and ratios with specific active ingredients, preferably if the active ingredients have a particular particle size.

The compound (B) is preferably a non-ionic surface-active compound or mixture of compounds having a hydrophile-lipophile balance (HLB) of between 10 to 18. Examples of non-ionic surface-active compounds (compound B) particularly suitable for the present invention include a polyoxyalkylene-sorbitan ester, castor oil alkoxylate, alcohol alkoxylate, fatty acid ethoxylate, fatty monoethanolamide based ethoxylate and block polymers of ethylene oxide and propylene oxide block.

In an embodiment, the polyoxyalkylene-sorbitan ester is ethoxylated, propoxylated, butoxylated and mixed ethoxy/propoxy and/or ethoxy/butoxy analogues having a C8-22 alkyl or alkenyl group and up to 20 ethlyleneoxy and/or propyleneoxy and/or butyleneoxy groups. A preferred polyoxyalkylene-sorbitan ester is ethoxylated sorbitan monoester (such as oleate or laurate), especially having on average 20 ethyleneoxy groups, which are ATPLUS 309 F (UNIQEMA), the ALKAMULS series (RHODIA) or TWEEN series (such as TWEEN 80, TWEEN 20, TWEEN 21) (CRODA-UNIQEMA). In a preferred embodiment, the polyoxyalkylene-sorbitan ester has a HLB between 11 and 17 such as between 12 and 17, especially 14 to 17, and preferably the saponification number being 45 to 55.

In an embodiment, the alcohol alkoxylate has an average molecular weight of less than 10000, more preferably less than 7000, especially less than 5000, such as in the range of 200 to 3500. Suitable examples are preferably polyethoxylated, saturated and unsaturated aliphatic alcohols, having 8 to 24 carbon atoms in the alkyl radical, which is derived from the corresponding fatty acids or from petrochemical products, and having 1 to 100, preferably 2 to 50, ethylene oxide units (EO), it being possible for the free hydroxyl group to be alkoxylated, which are commercially available, for example as GENAPOL X, GENAPOL OA, GENAPOL OX, GENAPOL UD, GENAPOL LA and GENAPOL 0 series (CLARIANT), CROVOL M series (CRODA) or as LUTENSOL series (BASF), or are obtainable therefrom by etherification, for example GENAPOL X080. A preferred surface active compound is an oleylpolyglycol ether, such as with 8 to 20 ethylene oxide units (for example, GENAPOL O100, SYNPERONIC A20) and a tridecyl alcohol ethoxylate. In a preferred embodiment, the polyalkoxylated alcohol alkoxylate has a HLB of between 10 and 13, preferably from 10.5 and 12.

In an embodiment, the castor oil alkoxylate is castor oil ethoxylate having preferably 30 to 45 EO groups, such as 30 to 35 EO groups. Examples include the AQNIQUE CSO series (COGNIS), TOXIMUL series(such as TOXIMUL 8240) (STEPAN) and ALKAMULS EL series (RHODIA). In a preferred embodiment, the HLB of the castor oil alkoxylate is between 10 and 14, such as between 11 and 13, and preferably the saponification number being 65 to 75, such as 67 to 71, mg KOH/g.

In an embodiment, the fatty acid ethoxylate is an ethoxylated fatty acid, such as oleic acid, having 10 to 30 EO groups, preferably 10 to 20 EO groups. Examples include NINEX series (such as NINEX MT-615) (STEPAN) and AGNIQUE FAC series (COGNIS). In a preferred embodiment, the HLB of the fatty acid ethoxylate is between 11 and 15, such as between 12 and 14.

In an embodiment, the fatty monoethanolamide based ethoxylate has C12 to C22 saturated or unsaturated acid alkyl chain with 10 to 40 EO groups. Examples include the NINOL series (STEPAN) and the AGNIQUE AAM (COGNIS) series. Preferably the HLB is 10 to 18, such as between 11 and 15, such as between 12 and 14.

In an embodiment, block polymers of ethylene oxide and propylene oxide block can be di- and tri-block copolymers, such as ABA or BAB block copolymer or BA block copolymers. Examples include the GENAPOL PF series (CLARIANT), the PLURONIC series (BASF), the SYNPERONIC PE series (UNIQEMA), or the TOXIMUL series (STEPAN). A preferred group of ethylene oxide/propylene oxide block copolymers for use in the compositions of this invention are butyl based poly(oxypropylene) poly(oxyethylene) block copolymers having an average molecular weight in a range of 2,400 to 3,500 (e.g. TOXIMUL 8320, Stepan Chemical Co.). Suitable examples include Pluronic L10, Pluronic L44, Pluronic L63, Pluronic L64, Pluronic P84, Pluronic P104, Pluronic P105, Step-Flow 26, Toximul 8323, and Toximul 8320. Preferably the HLB is 10 to 18, such as 11 to 16.

Preferred surface active compounds (B) are sorbitan ester ethoxylates, castor oil ethoxylates, fatty acid ethoxylates and fatty alcohol ethoxylates.

In an embodiment,
  the sorbitan ester ethoxylate is an ethoxylated sorbitan oleate having 20 ethyleneoxy groups and having a HLB between 11 and 17 such as between 12 and 17, especially 14 to 17;
  the castor oil ethoxylate has 30 to 45 EO groups, such as 30 to 35 EO groups and having a HLB of between 10 and 14, such as between 11 and 13;
  the fatty acid ethoxylate is a oleic acid having 10 to 30 EO groups, preferably 10 to 20 EO groups and having a HLB of between 11 and 15, such as between 12 and 14; and
  the fatty alcohol ethoxylate is a saturated or unsaturated aliphatic alcohol having 8 to 24 carbon atoms in the alkyl radical, which is derived from the corresponding fatty acids or from petrochemical products, and having 1 to 100, preferably 2 to 50, ethylene oxide units (EO) and having a HLB of between 10 and 13, preferably from 10.5 and 12.

In an embodiment, the amount of surface active compound (B) in a formulation is at least 6.5 to 25, preferably 7 to 20, preferably in the range of from 7 to 18, weight %, based on the total weight of the formulated composition.

In an embodiment, the ratio of surface active compound (B) to the active ingredient (A) is in the range of from 1.6 to 10.0, preferably 1.7 to 7.0.

In an embodiment, the amount of active ingredient (A), especially abamectin, is in the range of from 1.5 to 15, preferably 1.5 to 10, especially 2 to 9, weight %, based on the total weight of the formulated composition.

In an embodiment, the amount of active ingredient (A) is in the range of 6 to 10, preferably 7 to 9, weight % and the ratio of (B) to (A) is in the range of from 1.5 to 3.0, preferably 1.7 to 2.5. In such an instance, the active ingredient is preferably abamectin and surface active compound is preferably a sorbitan ester ethoxylate.

In an embodiment, the amount of active ingredient (A) is in the range of 2 to 5, preferably 2.5 to 4.5, weight % and the ratio of (B) to (A) is in the range of from 4.0 to 8.0, preferably 5.0 to 6.5. In such an instance, the active ingredient is preferably abamectin and surface active compound is preferably a sorbitan ester ethoxylate and optionally a second active ingredient (D) is also present.

In an embodiment, the amount of active ingredient (A) is in the range of 2 to 5, preferably 2.5 to 4.5, weight % and the ratio of (B) to (A) is in the range of from 4.0 to 7.0, preferably 4.5 to 5.5. In such an instance, the active ingredient is preferably abamectin and surface active compound is preferably a sorbitan ester ethoxylate and optionally a second active ingredient (D) is also present.

In an embodiment, the amount of active ingredient (A) is in the range of 1.0 to 3.0, preferably 1.5 to 2.5, weight % and the ratio of (B) to (A) is in the range of from 2.5 to 7.0, preferably 4.0 to 5.5. In such an instance, the active ingredient is preferably abamectin and surface active compound is preferably a sorbitan ester ethoxylate and optionally a second active ingredient (D) is also present.

In an embodiment, the amount of active ingredient (A) is in the range of 1.0 to 3.5, preferably 1.5 to 3.0, weight % and the ratio of (B) to (A) is in the range of from 2.0 to 6.0, preferably 3.0 to 5.0. In such an instance, the active ingredient is preferably abamectin and surface active compound is preferably a sorbitan ester ethoxylate and optionally a second active ingredient (D) is also present.

The correct choice of suitable formulation auxiliary components for the formulation often determines to a significant extent whether the active ingredient can display its full efficacy after application. When selecting suitable ingredients to ensure the physicochemical stability of the formulation, it must be taken into account that not every active ingredient can be processed into any given formulation type without losses in stability and/or efficacy. The appropriate choice and amount of other the customary formulation auxiliaries, such as surfactants, wetting agents, anti-foam, anti-freeze, thickener, pH buffer, preservative, etc is known to a skilled person realising that a formulated composition comprising (A) and (B), and optionally one or more further active ingredients, is to be formulated in a water-based composition.

In an embodiment, it has been found that the formulation defined in the first aspect benefits also from presence one or more other surface compounds different to (B), designated hereinafter as surface compound (C). In a preferred embodiment, surface compounds (C) are alkoxylated polyarylphenols and alkoxylated polyarylphenol phosphates.

In an embodiment, the alkoxylated polyarylphenol is a polyethoxylated, arylalkylphenols, such as, for example, 2,4,6-tris(1-phenylethyl)phenol (tristyrylphenol) having an average degree of ethoxylation of between 10 and 80, preferably from 16 to 40, such as SOPROPHOR BSU (RHODIA). Also suitable are EO/PO block copolymers of polyarylphenols, such as SOPROPHOR 796/P(RHODIA) and STEP-FLOW 1500 (STEPAN).

Examples of a phosphate type surfactant include an alkylphenol polyalkoxyether phosphate, a block copolymer of polyalkoxyether phosphate, a polyarylphenol polyalkoxyether phosphate and an arylphenol polyalkoxyether phosphate, such as SOPROPHOR 3D33 (RHODIA).

In a preferred embodiment, the formulated composition of the first aspect further comprises, as a surface active compound (C), an ethoxylated tristyrylphenol and/or an ethoxylated tristyrylphenol phosphate.

In an embodiment, each surface active (C) is present in an amount of at most 3, preferably 2.8, such as 0.5 to 2.5, weight %, based on the total weight of the formulation.

In the instance there are two or more surface active compounds (C) present, the ratio of any two, preferably non-ionic (C) to ionic (C), is in the range of 1:3 to 3:1, such as 2:5 to 4:2, preferably 1:2. to 3:2. Preferably the ionic surface active compound (C) is anionic, such as an ethoxylated (tristyrylphenol phosphate) and the non-ionic surface active compound (C) is an ethoxylated 2,4,6-tris(1-phenylethyl)phenol (tristyrylphenol).

In an embodiment, the formulation of the first aspect also benefits from one or more oil inerts, such as medium chain triglycerides (such as STEPAN 108) and rape seed oil methyl ester (such as STEPOSOL ROE-W).

The formulation of the present invention may further comprise other formulation auxiliaries known in the art of agrochemical formulations in customary amounts. Such auxiliaries include, but are not limited to, surfactants (such as anionic, non-ionic, cationic), antifreeze agents (such as but not limited to glycerine, ethylene glycol, propylene glycol, monopropylene glycol, hexylene glycol, 1-methoxy-2-propanol, cyclohexanol), buffering agents (such as but not limited to sodium hydroxide, phosphoric acid), preserving agents (such as but not limited to derivatives of 1,2-benzisothiazolin-3-one, benzoic acid, sorbic acid, formaldehyde, a combination of methyl parahydroxybenzoate and propyl parahydroxybenzoate), stabilizing agents (such as but not limited to acids, preferably organic acids, such as dodecylbenzene sulfonic acid, acetic acid, propionic acid or butyl hydroxyl toluene, butyl hydroxyl anisole), thickening agents (such as but not limited to heteropolysaccharide and starches), and antifoaming agents (such as but not limited to those based on silicone, particularly polydimethylsiloxane). Such auxiliaries are commercially available and known in the art.

In an embodiment, the formulation according to the first aspect further comprises one or more other active ingredients (D) different from (A). The other active ingredient can be of any type (e.g. herbicide, fungicide, insecticide, nematicide, etc), and can be of the same type as the active ingredient (A).

Examples of suitable other active ingredient include thiamethoxam, imidacloprid, clothianidin, tefluthrin, cyflumetofen, chlorantraniliprole, cyantraniliprole, difenconazole, fipronil, azoxystrobin and fludioxonil.

In an instance, the formulated composition comprises abamectin, and one or more selected from thiamethoxam, imidacloprid, clothianidin, lufenuron, lambda cyhalothrin, tefluthrin, cyflumetofen, chlorantraniliprole, cyantraniliprole, difenconazole, fipronil, azoxystrobin and fludioxonil.

The amount of the other active ingredient (D) can be from 1 to 30, preferably 2 to 20, such as 5 to 15, weight %, based on the total weight of the formulation.

In an embodiment, the formulation comprises abamectin and thiamethoxam. In an embodiment, the formulation comprises abamectin and chlorantraniliprole.

In an embodiment, the formulation comprises abamectin and cyantraniliprole.

In the instance of a mixture of active ingredients, the ratio of the other active ingredient (D) to active ingredient (A) can be 1:1 to 8:1, preferably 2:1 to 6:1.

In an embodiment, the formulation comprises abamectin and thiamethoxam, wherein ratio of thiamethoxam to abamectin is in the range of from 3.0 to 5.5, abamectin is present in an amount of according 2.5 to 4.5 weight %, and the ratio of (B) to (A) is in the range of 5.0 to 6.5.

In an embodiment, the formulation comprises abamectin and chlorantraniliprole, wherein ratio of chlorantraniliprole to abamectin is in the range of from 2.0 to 3.0, abamectin is present in an amount of 1.5 to 2.5 weight %, and the ratio of (B) to (A) is in the range of 4.0 to 5.5.

In an embodiment, the formulation comprises abamectin and chlorantraniliprole, wherein ratio of chlorantraniliprole to abamectin is in the range of from 3.5 to 4.5, abamectin is present in an amount of 1.5 to 3.0 weight %, and the ratio of (B) to (A) is in the range of 3.0 to 5.0.

In an embodiment, the formulation comprises abamectin and thiamethoxam, wherein the ratio of thiamethoxam to abamectin is in the range of from 1.5 to 2.5, abamectin is present in an amount of 3 to 9 weight %, and the ratio of (B) to (A) is in the range of 2 to 7, preferably 2.5 to 5.5.

The process for preparing the formulations of the invention are customary, and involves grinding the solid particles, such the active ingredient(s), optionally with formulation auxiliaries, with a mill to obtain the desired particle size and then combining with formulation auxiliaries and solvent. In an embodiment, horizontal bead mill such as a Netzsch zeta mill is advantageous. The mill media is composed of either glass, ceramic, ceria stabilized ceramic, or yttria stabilized ceramic beads in the size range of 0.3 mm-1.2 mm. Other types of milling equipment used include Drais mill, dyno mill, and/or an attritor. The solid particles size are reduced by passing the formulation through a grinding chamber where the media is circulated at high speeds in order to fracture the particles. In the case of a mixture of solid active ingredients, the active ingredients can be milled together, or separately and then combined to arrive at the formulation.

Generally the formulated compositions can be prepared as follows:

Technical grade active ingredient (compound A) is added, in solid form, to an aqueous solution containing at least one surfactant that suitably wets the solid, allowing for a concentrated crude suspension (typically 20-60 wt. % active ingredient). This solution may contain multiple surfactants to aid in dispersion and lubrication of the particles in the milling process, as well as components such as antifoam, antifreeze, pH adjusters and preservative. This suspension is mixed thoroughly with a suitable mixing device such as a Cowles blade or rotor-stator mixer before particle size reduction via milling.

The milling process, depending on the equipment used and the active ingredient being milled, can be carried out with a single mill, or alternatively multiple devices where the initial particle size is reduced with one mill, and ground to finer sizes with another mill. Appropriate devices for the first step of the two-step scenario include attritors, colloid mills, Dyno-mills and Eiger mills where milling media may consist of a variety of compositions and the media sizes are generally greater than 1 mm (nominally spherical beads). Appropriate devices for the second step of the two-step scenario include high-energy mills such as the Netzsch Lab Mini Zeta and the Drais Superflow. Milling media for these devices typically have diameters 1 mm or below and can consist of hard, dense materials such as yttrium.

Milling of the suspension from crude to fine particle sizes can be carried out by either recirculating the fluid or subjecting the fluid to multiple passes through the milling chamber, depending on the nature of the milling device. As the particle size of the solids is reduced, heat is generated, requiring cooling of the suspension.

Once the desired particle size of this suspension, as measured by an appropriate light scattering device, is achieved, it is either ready for subsequent formulation to the composition of the invention or can be further stabilized through use of a thickener such as a xanthan gum. This suspension is referred to as a "millbase".

The final formulated composition concentrate is formulated with appropriate components such as water, antifoam, antifreeze, preservatives, rheology modifiers and suspension aids, additional surfactants that serve to disperse the solids in concentration and when applied in dilute form, and in the case of the present invention, a non-ionic surface active compound defined in the first aspect (compound B), and optionally with millbases of other active ingredients. Mixing is typically achieved with standard impellers that allow for appropriate bulk agitation, and where necessary, higher shear dispersion. In the instance that a second millbase composition is of a capsule suspension, a formulator would take appropriate known precautions (such as the avoidance of high shear) to ensure capsule integrity. In some instances, a mixture of active ingredients may be co-milled together (e.g., abamectin and chlorantraniliprole) form a desired particle size of the suspension mixture and then this millbase formulated with other formulation auxiliaries to result in a formulation composition according to the invention.

The order of addition of the final formulation components can vary and depends on a number of factors, including available equipment and time required to mix certain components.

In a preferred embodiment, a formulation defined in the first aspect has suspended particles of active ingredient (A) having a size of from 0.1 to 0.9, preferably 0.4 to 0.8, especially 0.5 to 0.8, μm, at $x_{50}$ as defined in ISO 13320-1, which is incorporated by reference.

In a preferred embodiment, a formulation defined in the first aspect has suspended particles of active ingredient (A) having a size of from 0.7 to 1.5, preferably 0.9 to 1.5, especially 1.0 to 1.4, μm, at $x_{95}$ as defined in ISO 13320-1

The particle size of a second or further active ingredient (D90) may be the same or different from the particle size of the active ingredient (A). In an embodiment, the particle size of chlorantraniliprole is from 0.1 to 0.9, preferably 0.1 to 0.8, especially 0.15 to 0.8, μm, at $x_{50}$ as defined in ISO 13320-1.

In an embodiment, the particle size of chlorantraniliprole is from 0.1 to 0.9, preferably 0.4 to 0.8, especially 0.5 to 0.8, μm, at $x_{50}$ as defined in ISO 13320-1.

Further, the particle size of the formulated composition could differ from the particle size of the desired active ingredient (A) because the formulated composition has other solid or dispersed components, such as colorants and other solid active ingredients (D).

In an embodiment, the particle size of the formulated composition is 0.7 to 1.5, preferably 0.9 to 1.5, especially 1.0 to 1.4, μm, at $x_{95}$ as defined in ISO 13320-1, and independently of the $x_{95}$ size, a particle size of 0.1 to 0.9, preferably 0.4 to 0.8, especially 0.5 to 0.8, μm, at $x_{50}$ as defined in ISO 13320-1.

In an embodiment, the formulation according to the first aspect is in the form of a suspension concentrate or suspoemulsion.

Whereas commercial formulations will be formulated as concentrates (known as a pre-mix composition (or concentrate, formulated compound (or product)), the end user (e.g., farmer, grower or plant propagation material treater) will normally employ them after dilution with a solvent (such as water), optionally also containing one or more other pesticide pre-mixes and formulation auxiliaries. The diluted version of the pesticidal compositions is known as a tank mix composition (or ready-to-apply, spray broth, or slurry). The end user of the pesticidal composition can also use the commercial pesticidal compositions (formulations) without further dilution in certain circumstances. Accordingly, a pesticidal composition as used herein refers to a pre-mix composition or a tank mix composition.

As with the nature of the formulations, the methods of application, such as foliar, drench, spraying, atomizing, dusting, scattering, coating or pouring, are chosen in accordance with the intended objectives and the prevailing circumstances.

The tank-mix compositions are generally prepared by diluting with a solvent (for example, water) the one or more pre-mix compositions containing different pesticides, and optionally further auxiliaries.

Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

Generally, a tank-mix formulation for foliar or soil application comprises 0.1 to 20%, especially 0.1 to 15%, active ingredient compound(s), and 99.9 to 80%, especially 99.9 to 85%, of a solid or liquid auxiliaries (including, for example, a solvent such as water), where the auxiliaries can be a surfactant in an amount of 0 to 20%, especially 0.1 to 15%, based on the tank-mix formulation.

Normally, a tank-mix formulation for seed treatment application comprises 0.25 to 80%, especially 1 to 75%, active ingredient compounds, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

The formulated compositions according to the present invention can therefore also be used in combination with other pesticidal formulations, formulation auxiliaries, and adjuvants (a substance which in itself doesn't show pesticidal activity—usually crop oil concentrates and mixture of surfactants).

In an embodiment, non-ionic adjuvants are preferred for use with the pesticidal compositions of the invention.

Examples of non-ionic adjuvants product ranges include ATPLUS™, ATPLUS™ MBA, BRIJ,™ SYNPERONIC™, ATLAS™ G, ATLOX™, TWEEN™, and CROVOL™. Specific examples include PENETRATOR™, PENETRATOR Plus™, ADIGOR™, AGORA™, ATPLUS™ 411F, ATPLUS™ 463, SILWET™ L77, ATLOX™ SEMKOTE E-135, ALKAMUL™ BR, TURBOCHARGE™ D, CET SPEED™, DYNE-AMIC™.

Specific examples are:
DYNE-AMIC™ is a blend of highly refined vegetables oils combined with an organosilicone based surfactants.
ATPLUS 411 F is a mixture of paraffin based petroleum oil and a surfactant blend.
ATPLUS 463 is a blend of mineral oil and non-ionic surfactants.
PENETRATOR Plus is a mixture of light to mid range paraffin oil, polyol fatty acid esters, polyethoxylated esters thereof, ethoxylated alkyl aryl phosphate esters.
SILWET L-77 is a polyalkyleneoxide modified heptamethyltrisiloxane.
TURBOCHARGE D is a blend of mineral oil and non-ionic surfactants.
ALKAMUL BR is a castor oil ethoxylate 40.
CET SPEED is a blend of oleyl alcohol poylglycol ethers.
ADIGOR is a blend of petroleum distillates, methyl ester of fatty acids and alcohol ethoxylate.
AGORA is a blend of petroleum oil, alcohol and an emulsifier blend.
ATLOX SEMKOTE E-135 is an ethylene vinyl acetate terpolymer.

Use of certain adjuvants in a tank-mix composition containing certain pesticides offer unexpected benefits in respect of pesticide residue level management. Such adjuvants are non-ionic adjuvants as described herein. The pesticides are those defined in the first aspect, preferably abamectin.

The present invention provides a method of controlling or preventing pathogenic damage or pest damage. The present formulations and aqueous pesticidal suspension compositions may be of use for different purposes (such as foliar, soil or plant propagation material treatment) for the control of pathogenic and/or pest damage.

The pathogens and/or pests controlled would depend on the active ingredient(s) present in the applied composition.

The amount of active ingredient used for pathogenic and/or pest control would vary according to the specific active ingredient (e.g., abamectin is generally applied at a lower rate than lambda-cyhalothrin, nature of the soil, type of crop plant, prevailing climatic conditions, and can be determined by biology trials.

Typical application rate of abamectin to the locus of the crop plant is from 1 to 100 g per hectare (g/ha), such as 3 to 90 g/ha, especially from 6 to 60 g/ha, preferably from 9 to 36 g/ha, most preferably from 12 to 27 g/ha. The pesticide may be applied once or several occasions during the growth of a plant depending on the plant and circumstances, for example, 1 to 6 or 1 to 4 occasions (for a tomato crop harvest, for example, the combination can be applied up to 6 times before harvest), and the amounts indicated above are for each application.

The amount of active ingredient used on the propagation material varies according to specific active ingredient (e.g., abamectin is generally applied at a lower rate than lambda-cyhalothrin, type of propagation material (e.g., seed or tuber) and plant (for example, wheat seeds generally have less active ingredients adhered thereto than oil seed rape seeds based on equivalent weight of seeds) and is such that the defined pesticide particles is an effective amount to provide the desired pesticidal action and can be determined by biology trials.

The application rates can, therefore, range from 6 g to 250 kg of per 100 kg of seeds. Generally, the application rate for cereal seeds range from 23 g to 740 g, preferably 5 g to 600 g, per 100 kg of seeds; and the application rate for oil seed rape seeds can range from 700 g to 25 kg, preferably 1.5 kg to 20 kg, per 100 kg of seeds. Generally treatment rate of abamectin on to a cotton seed is in the range of 0.1 to 0.2 mg ai/seed, to a tomato seed is in the range of 0.3 to 0.6 mg ai/seed and to a soybean seed is in the range of 0.1 to 0.2 mg ai/seed.

Therefore, the present invention also provides a plant propagation material treated with the formulation and aqueous suspension composition defined in the first and second aspect respectively.

The present invention is especially suitable for agronomically important plants, which refers to a plant that is harvested or cultivated on a commercial scale.

Examples of such agronomic plants (or crops) are cereals, such as wheat, barley, rye, oats, rice, maize or sorghum; beet, such as sugar or fodder beet; fruit, for example pome fruit, stone fruit and soft fruit, such as apples, pears, plums, prunes, peaches, almonds, cherries or berries, for example strawberries, raspberries or blackberries; legumes, such as beans, lentils, peas or soya beans; oil crops such as oil seed rape, mustard, poppies, olives, sunflowers, coconuts, castor, cacao or peanuts; the marrow family, such as pumpkins, cucumbers or melons; fibre plants such as cotton, flax, hemp or jute; citrus fruits such as oranges, lemons, grapefruits or tangerines; vegetables such as spinach, lettuce, asparagus, cabbage species, carrots, onions, chillis, tomatoes, potatoes, or capsicums; the laurel family such as avocado, Cinnamonium or camphor; and tobacco, nuts (such as walnut), coffee, egg plants, sugar cane, tea, pepper, grapevines, hops, the banana family, latex plants and ornamentals. Also important are forage crops such as grassed and legumes.

Suitable target crops also include transgenic crop plants of the foregoing types. The transgenic crop plants used according to the invention are plants, or propagation material thereof, which are transformed by means of recombinant DNA technology in such a way that they are—for instance—capable of synthesizing selectively acting toxins as are known, for example, from toxin-producing invertebrates, especially of the phylum Arthropoda, as can be obtained from *Bacillus thuringiensis* strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

A description of the structure of the pesticides mentioned herein can be found in the e-Pesticide Manual, version 3.1, 13th Edition, Ed. CDC Tomlin, British Crop Protection Council, 2004-05.

In each aspect and embodiment of the invention, "consisting essentially" and inflections thereof are a preferred embodiment of "comprising" and its inflections, and "consisting of" and inflections thereof are a preferred embodiment of "consisting essentially of" and its inflections.

The following Examples are given by way of illustration and not by way of limitation of the invention.

EXAMPLES

Preparation Examples

P.1—Preparation of an Abamectin Millbase

In a suitably-sized vessel, polyarylphenol alkoxylate (Soprophor BSU, 28.4 g) and polyarylphenol alkoxylate phosphate (Soprophor 3D33, 18.9 g) were added to potable water (622.5 g) and mixed. Propylene glycol (94.7 g), antifoam (Antifoam 1510, 3.8 g) were further added with mixing, followed by Abamectin (900 g). The pH of the mixture was adjusted to approximately pH 6 using sodium hydroxide (25% in water, 1.2 g). The crude suspension was first passed through a Dyno-Mill (0.6 liter mill chamber volume) to reduce particle size of the suspended particles below 50 micrometers, followed by milling in recirculation mode on Netzsch Lab Mini Zeta IIE mill until the particle size of the suspended particles was below 1.5 micrometers ($X_{95}$).

P.2—Preparation of Example 2

In a suitably-sized vessel, propylene glycol (31.3 g), polyarylphenol alkoxylate (Soprophor BSU, 6.2 g), polyarylphenol alkoxylate phosphate (Soprophor 3D33, 22.5 g), polyoxyalkylene sorbitan ester (Tween 80, 127.7 g), preservative (Proxel GXL, 0.6 g) and antifoam (Antifoam 1510, 1.3 g) were mixed using a Cowles impeller. Potable water (442.0 g) and Abamectin millbase (P.1, 120.0 g) were added with continued mixing. Thickener (Kelzan, 1.9 g) was added with mixing for one hour to assure satisfactory dispersion. The pH of the suspension concentrate was adjusted to approximately 6 with sodium hydroxide (25% in water, 1.0 g).

P.3—Preparation of Example 13

Step 1: In a suitably-sized vessel, propylene glycol (119.2 g), polyarylphenol alkoxylate phosphate (Soprophor 3D33, 40.6 g) and polyarylphenol alkoxylate (Soprophor BSU, 20.1 g) were mixed to homogeneity. Potable water (517.1 g), antifoam (Antifoam 1500, 1.0 g) and potassium hydroxide (50% in water, 1.99 g) were further added with mixing, followed by an active ingredient (D) (287.4 g). The crude suspension was milled with a Netzsch Lab Mini Zeta IIE mill until the particle size of the suspended particles is below 1.2 micrometers ($X_{95}$) to yield a millbase of the active ingredient.

Step 2: Thereafter, in a suitably-sized vessel, propylene glycol (485.3 g), polyoxyalkylene sorbitan ester (Tween 80, 400.0 g), polyarylphenol alkoxylate phosphate (Soprophor 3D33, 59.1 g) and polyarylphenol alkoxylate (Soprophor BSU, 75.1 g) were mixed to homogeneity. Potable water, antifoam (Antifoam 1500, 13.1 g) potassium hydroxide (50% in water, 2.6 g), preservative (Proxel GXL, 12.5 g) were added with mixing followed by Abamectin millbase (P.1, 171.7 g) and millbase prepared in step 1 (30 wt. %, 750.2 g). Thickener (Rhodopol 23, 9.5 g) and suspending agent (Attaflow FL, 100.1 g) were added and mixed to fully disperse.

P.4—Preparation of Example 15

Step 1: In a suitably-sized vessel, potable water (3104.0 g), lignosulfonate (Borresperse NA, 61.2 g), propylene glycol (243.9 g), polyarylphenol alkoxylate phosphate (Soprophor 3D33, 175.5 g) and antifoam (Antifoam 1510, 30.9 g) were mixed with moderate agitation using a Cowles impeller. Active ingredient (D) (2442.3 g) was added until well-mixed. The pH of the crude suspension was adjusted with sodium hydroxide (25% in water, 8.6 g) to approximately 4.6. The suspension was milled with two passes through a Dyno-mill (0.6 liter mill chamber), resulting in particle size of 8.0 micrometers ($X_{95}$) to yield a millbase of the active ingredient.

Step 2: Thereafter, in a suitably-sized vessel, potable water (6700.0 g) and polyoxyalkylene sorbitan ester (Tween 80, 1996.0 g) were added with moderate agitation to homogeneity. Preservative (Proxel GXL, 8.1 g), millbase prepared in step 1 (2042.0 g) and Abamectin millbase (P.1, 819.6 g) and suspending agent (Attaflow FL, 236.0 g) were added and mixed with moderate agitation. Thickener (Rhodopol 23, 18.7 g) was slowly added with high agitation. The pH is adjusted to approximately 6.5 with sodium hydroxide (25% in water, 0.5 g) and the suspension concentrate was further mixed for one hour.

P.5—Preparation of Example E

Step 1: Thereafter, in a suitably-sized vessel, suspoemulsion (P.6, 62.49 g), potable water (52.73 g), preservative (Acticide GA, 0.23 g) and antifoam (Antifoam 1500, 0.19 g) were added with moderate agitation to homogeneity. Abamectin millbase (P.1, 4.33 g) was added and mixed with moderate agitation. The pH is adjusted to approximately 5.4 with sulfuric acid (85%, 0.05 g) and allowed to mix at moderate agitation. The suspending agent (Attaflow FL, 1.67 g) was added and mixed with moderate agitation. Thickener (Rhodopol 23, 0.30 g) was slowly added with high agitation and the suspension concentrate was further mixed for 30 minutes.

P.6—Preparation of Example 20

Step 1: In a suitably-sized vessel, polyarylphenol alkoxylate phosphate (Soprophor 3D33, 35.13 g) and polyarylphenol alkoxylate (Soprophor BSU, 34.74 g) were mixed to homogeneity. Potable water (442.0 g), antifoam (Antifoam 1500, 2.22 g) and potassium hydroxide (50% in water, 2.16 g) were further added with mixing, followed by an active ingredient (D) (475.8 g). The crude suspension was milled with a Netzsch Lab Mini Zeta IIE mill until the particle size of the suspended particles is below 1.8 micrometers ($X_{95}$) to yield a millbase of the active ingredient.

Step 2: Thereafter, in a suitably-sized vessel, potable water (80.0 g), polyarylphenol alkoxylate (Soprophor BSU, 40.4 g) and propylene glycol (32.0 g) were added with high shear mixing via a Silverson mixer (3.0 rpm) to homogeneity. Rape seed oil methyl ester (Steposol ROE-W, 48.0 g) was added slowly to a Silverson mixer at a rate of 3.5 rpm. Mixing continued at this rate for 4 minutes, resulting in particle size of 0.61 micrometers ($X_{95}$).

Step 3: Thereafter, in a suitably-sized vessel, suspoemulsion prepared in Step 2 (62.57 g), potable water (25.75 g), preservative (Acticide GA, 0.19 g) and antifoam (Antifoam 1500, 0.17 g) were added with moderate agitation to homogeneity. Millbase prepared in Step 1 (26.30 g) and Abamectin millbase (P.1, 4.28 g) and suspending agent (Attaflow FL, 1.54 g) were added and mixed with moderate agitation. Thickener (Rhodopol 23, 0.28 g) was slowly added with high agitation. The suspension concentrate was further mixed for 30 to 40 minutes or until homogeneous.

The remaining examples were prepared analogously with appropriate adjustments to active ingredients, inert concentrations and types, and particle sizes.

Examples J & K are commercial emulsifiable concentrates of abamectin—Example J is the US product known as AGRIMEK and Example K is the European product called VERTIMEC

TABLE 1

Examples of formulations (wt %)

| | A | 1 | B | 2 | C | D | 3 | 4 |
|---|---|---|---|---|---|---|---|---|
| Abamectin (component (A)) | 8.24 | 8.24 | 8.00 | 8.00 | 4.00 | 4.03 | 4.02 | 4.01 |
| a polyoxyalkylene-sorbitan ester having an HLB of 15 (component (B)) | — | 16.67 | — | 17.00 | — | — | 16.91 | 17.00 |
| a polyoxyalkylene-sorbitan ester having an HLB of 16 (component (B)) | — | — | — | — | — | — | — | — |
| alkoxylated polyarylphenol (component (C)) | 1.00 | 0.81 | 1.00 | 1.00 | 0.92 | 0.91 | 0.92 | 0.93 |
| alkoxylated polyarylphenol phosphate (component (C)) | 1.48 | 1.25 | 1.50 | 1.50 | 1.38 | 1.39 | 1.36 | 1.38 |
| antifreeze | 4.95 | 4.95 | 5.02 | 5.00 | 4.59 | 4.58 | 4.58 | 4.57 |
| antifoam | 0.20 | 0.20 | 0.20 | 0.25 | 0.20 | 0.21 | 0.21 | 0.18 |
| preservative | 0.06 | 0.06 | 0.08 | 0.10 | 0.09 | 0.10 | 0.08 | 0.09 |
| thickener | 0.13 | 0.13 | 0.15 | 0.25 | 0.24 | 0.27 | 0.24 | 0.27 |
| pH buffer | 0.25 | 0.12 | 0.12 | 0.11 | 0.10 | 0.07 | 0.10 | 0.10 |
| water | balance | balance | balance | balance | balance | balance | balance | balance |
| Particle size, x50 of component A (μm) | 3.0 | 3.0 | 0.7 | 0.7 | 2.07 | 0.57 | 0.57 | 2.07 |
| Particle size, x95 of component A (μm) | 12 | 12 | 1.5 | 1.5 | 9.87 | 1.35 | 1.35 | 9.87 |
| Particle size, x50 of formulation (μm) | 3.0 | 3.0 | 0.7 | 0.7 | 2.07 | 0.57 | 0.57 | 2.07 |
| Ratio of (B):(A) | — | 2.0 | — | 2.1 | — | — | 4.3 | 4.3 |

TABLE 2

Examples of formulations (wt %)

| | 5 | 6 | 7 |
|---|---|---|---|
| Abamectin (component (A)) | 4.02 | 4.00 | 8.0 |
| a polyoxyalkylene-sorbitan ester having an HLB of 15 (component (B)) | — | — | 17.00 |
| a polyoxyalkylene-sorbitan ester having an HLB of 16 (component (B)) | 16.98 | 16.91 | — |
| alkoxylated polyarylphenol (component (C)) | 0.90 | 0.92 | — |
| alkoxylated polyarylphenol phosphate (component (C)) | 1.39 | 1.38 | — |
| Complex organic phosphate ester, free acid | — | — | 1.00 |
| Block copolymer PO/EO | — | — | 1.00 |
| antifreeze | 4.58 | 4.57 | 5.00 |
| antifoam | 0.20 | 0.20 | 0.21 |
| preservative | 0.08 | 0.10 | 0.11 |
| thickener | 0.24 | 0.24 | 0.25 |
| pH buffer | 0.08 | 0.08 | 0.11 |
| water | balance | balance | balance |
| Particle size, x50 of component A (μm) | 0.57 | 2.07 | — |
| Particle size, x95 of component A (μm) | 1.35 | 9.87 | 1.5 |
| Particle size, x50 of formulation (μm) | 0.57 | 2.07 | — |
| Ratio of (B):(A) | 4.2 | 4.2 | 2.1 |

TABLE 3

Examples of formulations (wt %)

|  | 8 | E | 9 | 10 | F | 11 | 12 |
|---|---|---|---|---|---|---|---|
| Abamectin (component (A)) | 1.75 | 1.75 | 1.78 | 1.87 | 1.73 | 1.71 | 1.78 |
| a polyoxyalkylene-sorbitan ester having an HLB of 15 (component (B)) | 8.24 | — | — | — | — | — | — |
| Tall oil fatty acid having an HLB of 13 (component B) | — | — | 20.22 | — | — | — | — |
| Condensation product of castor oil and EO having an HLB of 13 (component B) | — | — | — | 9.97 | — | — | — |
| a polyoxyalkylene-sorbitan ester having an HLB of 13.3 (component (B)) | — | — | — | — | — | 8.33 | — |
| a polyoxyalkylene-sorbitan ester having an HLB of 16 (component (B)) | — | — | — | — | — | — | 8.27 |
| alkoxylated polyarylphenol (component (C)) | 1.84 | 10.11 | — | — | 1.87 | 1.87 | 1.85 |
| alkoxylated polyarylphenol phosphate (component (C)) | 2.00 | 0.06 | — | — | 1.86 | 1.87 | 1.88 |
| Rape seed oil methyl ester (an oil) | — | 12.13 | — | — | — | — | — |
| Medium chain triglycerides (an oil) | — | — | — | 11.97 | — | — | — |
| antifreeze | 11.47 | 9.56 | 21.43 | 9.87 | 11.64 | 11.65 | 11.65 |
| antifoam | 0.23 | 0.15 | 0.13 | 0.17 | 0.26 | 0.29 | 0.26 |
| preservative | 0.26 | 0.19 | 0.26 | 0.24 | 0.25 | 0.28 | 0.32 |
| thickeners | 2.22 | 1.60 | 1.43 | 1.70 | 2.25 | 2.31 | 2.69 |
| Base pH buffer | 0.23 | 0.004 | 0.004 | 0.004 | 0.09 | 0.05 | 0.04 |
| Acid pH buffer | — | 0.04 | 0.06 | 0.05 | — | — | — |
| water | balance | balance | balance | balance | balance | balance | balance |
| Particle size, x50 of component A | 0.57 | 0.57 | 0.57 | 0.57 | 0.57 | 0.57 | 0.57 |
| Particle size, x95 of component A | 1.35 | 1.35 | 1.35 | 1.35 | 1.35 | 1.35 | 1.35 |
| Particle size, x50 of formulation | 0.57 | 0.57 | 0.57 | 0.57 | 0.57 | 0.57 | 0.57 |
| Ratio of (B):(A) | 4.7 | — | 11.4 | 5.3 | — | 4.9 | 4.6 |

TABLE 4

Examples of formulations (wt %)

|  | 13 | 14 | 15 | 16 | G |
|---|---|---|---|---|---|
| Abamectin (component (A)) | 1.71 | 2.12 | 3.02 | 3.43 | 1.71 |
| co-active ingredient (component (D)) | 4.29* | 8.49* | 13.85+ | 6.86+ | 4.29 |
| a polyoxyalkylene-sorbitan ester having an HLB of 15 (component (B)) | 8.00 | 8.00 | 17.00 | 17.00 | — |
| alkoxylated polyarylphenol (component (C)) | 1.84 | 2.14 | 0.06 | 0.07 | 1.80 |
| alkoxylated polyarylphenol phosphate (component (C)) | 1.84 | 2.77 | 1.09 | 0.60 | 1.78 |
| lignosulfonate | 0 | 0 | 0.35 | 0.17 | — |
| antifreeze | 11.69 | 10.32 | 1.70 | 1.04 | 11.56 |
| antifoam | 0.29 | 0.30 | 0.20 | 0.12 | 0.28 |
| preservative | 0.25 | 0.25 | 0.25 | 0.25 | 0.25 |
| thickener | 0.19 | 0.19 | 0.15 | 0.16 | 0.19 |
| pH buffer | 0.08 | 0.11 | 0.30 | 0.31 | 0.08 |
| suspension aid | 2.00 | 1.94 | 1.91 | 2.00 | 2.00 |
| water | balance | balance | balance | balance | balance |
| Particle size, x50 of AI (A) | 0.5 | 0.5 | 0.5 | 0.5 | 0.5 |
| Particle size, x95 of AI (A) | 1.3 | 1.3 | 1.3 | 1.3 | 1.3 |
| Particle size, x50 of AI (D) | 0.5 | 0.5 | 2.9 | 2.9 | 0.5 |
| Particle size, x95 of AI (D) | 1.3 | 1.5 | 8.0 | 8.0 | 1.3 |
| Particle size, x50 (formulation) | 0.5 | 0.5 | 1.6 | 1.6 | 0.5 |
| Ratio of (B):(A) | 4.7 | 3.8 | 5.6 | 5.0 | — |

*chlorantraniliprole;
+thiamethoxam

TABLE 5

Examples of formulations (wt %)

|  | 17 | 18 | 19 | 20 | 21 | 22 | 23 | H |
|---|---|---|---|---|---|---|---|---|
| Abamectin (component (A)) | 1.71 | 1.75 | 1.75 | 1.75 | 1.75 | 1.75 | 1.75 | 1.75 |
| Cyantraniliprole (component (D)) | 5.98 | 8.75 | 8.75 | 8.75 | 8.75 | 8.75 | 8.75 | 8.75 |
| a polyoxyalkylene-sorbitan ester having an HLB of 15 (component (B)) | 20.04 | 20.13 | 20.14 | — | — | — | 8.29 | — |
| Tall oil fatty acid having an HLB of 13 (component B) | — | — | — | — | 20.05 | 20.32 | — | — |
| Condensation product of castor oil and EO having an HLB of 13 (component B) | — | — | — | 10.00 | — | — | — | — |
| a polyoxyalkylene-sorbitan ester having an HLB of 13.3 (component (B)) | — | — | — | — | — | — | — | — |

TABLE 5-continued

Examples of formulations (wt %)

|  | 17 | 18 | 19 | 20 | 21 | 22 | 23 | H |
|---|---|---|---|---|---|---|---|---|
| a polyoxyalkylene-sorbitan ester having an HLB of 16 (component (B)) | — | — | — | — | — | — | — | — |
| alkoxylated polyarylphenol (component (C)) | 0.53 | 0.77 | 0.79 | 0.79 | 0.78 | 0.79 | 2.57 | 11.00 |
| alkoxylated polyarylphenol phosphate (component (C)) | 0.55 | 0.79 | 0.81 | 0.81 | 0.80 | 0.81 | 2.38 | 0.81 |
| Rape seed oil methyl ester (an oil) | — | — | — | — | — | — | — | 12.26 |
| Medium chain triglycerides (an oil) | — | — | — | 10.00 | — | — | — | — |
| antifreeze | 20.96 | 21.00 | 20.97 | 9.34 | 20.82 | 21.02 | 4.98 | 9.57 |
| antifoam | 0.17 | 0.18 | 0.23 | 0.14 | 0.18 | 0.18 | 0.31 | 0.18 |
| preservative | 0.20 | 0.25 | 0.24 | 0.23 | 0.24 | 0.23 | 0.23 | 0.21 |
| thickeners | 1.22 | 1.18 | 1.25 | 1.21 | 1.17 | 1.25 | 1.91 | 1.21 |
| Base pH buffer | 0.04 | 0.06 | 0.06 | 0..06 | 0.06 | 0.06 | 0.19 | 0.06 |
| Acid pH buffer | 0.05 | 0.10 | 0.02 | 0.45 | 0.09 | 0.29 | 0.02 | 0.02 |
| water | balance | balance | balance | balance | balance | balance | balance | balance |
| Particle size, x50 of component A | 0.57 | 0.57 | 0.57 | 0.57 | 0.57 | 0.57 | 0.57 | 0.57 |
| Particle size, x95 of component A | 1.35 | 1.35 | 1.35 | 1.35 | 1.35 | 1.35 | 1.35 | 1.35 |
| Particle size, x50 of component D | 0.48 | 1.06 | 0.48 | 0.48 | 1.06 | 0.48 | 0.48 | 0.48 |
| Particle size, x95 of component D | 1.80 | 11.80 | 1.80 | 1.80 | 11.80 | 1.80 | 1.80 | 1.80 |
| Ratio of (B):(A) | 11.7 | 11.5 | 11.5 | 5.7 | 11.5 | 11.6 | 4.7 | — |

Dilution Tests:

Dilution tests were carried out room temperature. Using an Eppendorf pipette, 4 mL of each formulation was diluted into 96 mL of water in a 100 mL glass graduated cylinder. The water having different levels of water hardness, e.g. 50 ppm, 342 ppm and 1000 ppm corresponding to concentrations of divalent ions (namely calcium and magnesium) was used. The time intervals were chosen to simulate diluted product standing over a typical "break" for the applicator (1, 2 or 4 hours) and overnight (24 hours). The dilutions were inverted 20× and allowed to stand. After standing for the desired time, the cylinders were noted for the volume of settled sediment and after the 24 hour reading they were subsequently subjected to cycles of inversions until the bottom of each cylinder was visually free of sediment. Inversions were performed manually (see Table X & Y for the results).

TABLE X

| Example | Active ingredient (A) Particle size (D95/D50, in microns) | Water hardness for dilutions (ppm) | Sediment (mL) 1 Hour | 4 Hours | 24 Hours | % serum | # reinversions after standing overnight |
|---|---|---|---|---|---|---|---|
| 3 | 1.35/0.57 | 50 | — | — | — | — | 2 |
| 3 | 1.35/0.57 | 342 | — | — | — | — | 2 |
| 3 | 1.35/0.57 | 1000 | — | — | — | — | 2 |
| 4 | 9.87/2.07 | 50 | — | — | — | 1.0 | 15 |
| 4 | 9.87/2.07 | 342 | — | — | 0.5 | 1.5 | 11 |
| 4 | 9.87/2.07 | 1000 | — | — | 0.5 | 1.5 | 13 |
| 5 | 1.35/0.57 | 50 | — | — | — | — | 7 |
| 5 | 1.35/0.57 | 342 | — | — | — | — | 4 |
| 5 | 1.35/0.57 | 1000 | — | — | 0.25 | — | 7 |
| 6 | 9.87/2.07 | 50 | — | — | 0.5 | 1.0 | 8 |
| 6 | 9.87/2.07 | 342 | — | — | 0.75 | 1.0 | 6 |
| 6 | 9.87/2.07 | 1000 | — | trace | 0.5 | 1.0 | 10 |
| D | 1.35/0.57 | 50 | — | — | — | — | 10 |
| D | 1.35/0.57 | 342 | — | — | — | — | 10 |
| D | 1.35/0.57 | 1000 | — | — | — | — | 10 |
| C | 9.87/2.07 | 50 | — | — | — | 1.0 | 14 |
| C | 9.87/2.07 | 342 | — | — | 0.25 | 1.0 | 12 |
| C | 9.87/2.07 | 1000 | — | — | 0.5 | 1.0 | 16 |

TABLE Y

| Example | active ingredient (D) particle Size (D95, D50 in microns) | active ingredient (A) particle size (D95, in microns) | Water hardness for dilutions (ppm) | Sediment, 1 hr in mL | Sediment, 2 hr in mL | Sediment, overnight, in mL | # reinversions after standing overnight |
|---|---|---|---|---|---|---|---|
| 12 | 8.52, 1.07 | 1.16 | 50 | nil | nil | trace | 22 |
| 12 | 8.52, 1.07 | 1.16 | 1000 | trace | trace | 1.5 | 12 |
| G | 8.52, 1.07 | 1.16 | 50 | trace | trace | trace | 31 |
| G | 8.52, 1.07 | 1.16 | 1000 | trace | trace | 0.5 | 12 |
| 12(2) | 4.56, 0.69 | 1.16 | 50 | nil | trace | trace | 23 |
| 12(2) | 4.56, 0.69 | 1.16 | 1000 | nil | 0.25 | 2.5 | 5 |
| G(2) | 4.56, 0.69 | 1.16 | 50 | nil | trace | trace | 20 |
| G(2) | 4.56, 0.69 | 1.16 | 1000 | trace | 0.25 | 3 | 9 |
| 12(3) | 1.34, 0.17 | 1.16 | 50 | nil | nil | trace | 6 |

TABLE Y-continued

| Example | active ingredient (D) particle Size (D95, D50 in microns) | active ingredient (A) particle size (D95, in microns) | Water hardness for dilutions (ppm) | Sediment, 1 hr in mL | Sediment, 2 hr in mL | Sediment, overnight, in mL | # reinversions after standing overnight |
|---|---|---|---|---|---|---|---|
| 12(3) | 1.34, 0.17 | 1.16 | 1000 | nil | nil | 0.25 | 6 |
| G(3) | 1.34, 0.17 | 1.16 | 50 | nil | nil | trace | 8 |
| G(3) | 1.34, 0.17 | 1.16 | 1000 | nil | trace | 0.5 | 8 |

Note:
Examples 12(2), 12(3) correspond compositionally to Example 12 and Examples G(2) and (G3) correspond compositionally to Example G, but the milling of the active ingredient (D) composition varied before admixing with the composition containing active ingredient (A).

Example B1

Translaminar Test Against Two Spotted Spider Mite *Tetranychus urticae* on French Beans (*Phaseolus vulgaris*)

The underside of 2 week old bean plants was infested with a mixed population of *T. urticae*. The border of the underside of the leaves is surrounded with a gum barrier to prevent the mites to move to the upper side of the leaves. One day after the infestation plants were treated with a track sprayer from the top with 200 L/ha of Example 2 products containing different amounts of Penetrator Plus. Plants were incubated in the greenhouse for 9 days and the evaluation was done on mortality against eggs and mobile stages (see Table A for the results of ABA efficacy).

Example B2

Control of *Tetranychus* Sp. Adults on Vegetables

In a plot size of 14 m2, two foliar spray applications of each composition were made at a treatment rate of 9 grams/ha (second was 7 days after the first application). Each treatment was done in three replicates. Each adjuvant was added to Example 1 in a tank-mix based on 17 ml product/ha. First application was conducted 71 days after transplanting and the evaluation was done on mortality against mobile stages by taking 20 leaves from each plot at different intervals (see Table B for the results).

Example B3

Control of Colorado Potato Battle on Potatoes

In a plot size of 7.5 m2, one foliar spray application of each composition were made at a treatment rate of 1 grams/ha. Each treatment was done in three replicates. Each adjuvant was added to Example 1 in a tank-mix based on 2 ml product/ha. The application was conducted 53 days after planting and the evaluation was done on mortality against larvae by counting the live larvae present per plot at different intervals and converting the data in % of control (see Table C for the results).

Example B4

Control of *Liriomyza trifolii* Pupae on Chrysanthemums

CHRYSANTHEMUMS potted plants were infested with a very high population of adult leafminers allowing them to lay eggs. Four days after the initial infestation plants were sprayed using a CO2 compressed backpack sprayer with an application volume of 1800 L/ha. Plants were incubated in the greenhouse for 9 days after the application and the evaluation was done by counting the number of pupae per plant obtained for each treatment (see Table D for the results).

Example B5

Residue Study

In a plot size of 25 ft×5 ft with 2 rows of Romaine lettuce (30" row spacing, 8" plant spacing so ~70 plants/plot), a single application of a treatment listed in Table below was made as a post foliar broadcast spray at a rate of 0.038 lb. a.i. per acre. Each treatment was done in two replicates with a control in each replicate. A minimum of ~3 lb of lettuce leaves were collected for each sample. Samples were harvested at 0, 0.25 (corresponding to 6 hrs), 3, 7, 14 and 21 days after last application (DALA). The O-DALA samples were harvested as soon as the spray dried. Samples were transported frozen and were prepared by grinding the samples with dry ice using a tabletop mill. The abamectin residue was analysed using a HPLC-Fluorescence Method (see Table E for the results).

| Treatment | Application | Application Type | GPA |
|---|---|---|---|
| 1 | Control | — | — |
| 2 | Example J (comparative) | Post foliar broadcast/on the day of harvest of mature leaves | 29.5 |
| 3 | Example A | Post foliar broadcast/on the day of harvest of mature leaves | 29.9 |
| 4 | Example 2 | Post foliar broadcast/on the day of harvest of mature leaves | 30.5 |
| 5 | Example J & Dyne-Amic ® at 0.25% v/v | Post foliar broadcast/on the day of harvest of mature leaves | 29.7 |
| 6 | Example A & Dyne-Amic ® at 0.25% v/v | Post foliar broadcast/on the day of harvest of mature leaves | 30.1 |
| 7 | Example 2 & Dyne-Amic ® at 0.25% v/v | Post foliar broadcast/on the day of harvest of mature leaves | 29.9 |

Example B6

UV Degradation Study

Photostability was assessed using an Atlas SUNTEST XLS+ unit (Part number 55007820) which utilises a xenon arc-lamp and a Special UV-filter (Part number 56052371) to simulate natural sunlight in both spectrum and intensity.

Treatments were diluted either in ultra-pure water (or in ultra-pure water containing 0.1% Penetrator Plus) to give dilutions that were 125 ppm wrt abamectin. 8×2 ul drops were dispensed using a Hamilton PB600 repeating dispenser fitted with a glass 100 μl Hamilton syringe onto pre-scored glass microscope slides—typically seven or eight for each treatment. These were allowed to dry prior to being covered with clean UV transparent silica slides to minimise volatile loss from the deposit. One slide for each compound was not irradiated and designated as time zero (T0). The other prepared slides were placed in the SUNTEST XLS+ on a water-cooled sample table (attached to a circulating water bath set to 15° C.) and irradiated for time periods ranging from 30 minutes up to 43 hours.

To quantify the amount of compound remaining, one slide was removed for each treatment from the SUNTEST unit, broken in half across the shaft of a small spatula, sandwiched with the clean sides together and placed in a 60 ml wide necked glass screw topped jar. The silica slide was rinsed with 2×2.5 mls of 50:50 (80/20 MeCN/THF): 0.1% H3PO4 into the jar, the lid replaced and the jar sonicated for 30 minutes. All jars were left standing at room temperature in covered boxes prior to analysis by LC with MS detection without further preparation (see Table F for the results).

Example B7

Two golden Delicious apple plants grown outside in a propagation container (1-2 years old) were treated with the products. The treatment areas for new and old leaves were defined and marked before product application. A horizontal band was marked on each leaf (approximately ¾ of the way down from the leaf tip) with a permanent marker pen. All treatments were applied using a hand held pipette to the marked areas on each leaf as 10×0.5 ul droplets (corresponding to 25 ug Al per leaf) with four replicate leaves per treatment, and the plants left outside. The products were AGRIMEK, Example 2, and Example 2 with 0.25% v/v Horticultural spray oil (i.e summer oil). After 1, 3 and 6 days after treatment, abamectin residues were assessed either on the leaf surface or inside the leaf tissue on all four leaves per product treatment. Surface analysis involved washing the leaf with acetone, followed by a chloroform and then LCMS, while inside the leaf tissue analysis involved freezing the leaves, homogenising in 5 ml acetone, centrifuging and 1 ml of the resulting supernatant used for LCMS analysis (see Table G & H for the results).

TABLE A control of *Tetranychus urticae*

| ABA a.i ppm | Varying amounts of Penetrator Plus, based on %, v/v | | | |
|---|---|---|---|---|
| | 0 | 0.05 | 0.1 | 0.2 |
| 12.5 | 35 | 100 | 100 | 100 |
| 3 | 0 | 97 | 100 | 100 |
| 0.8 | 0 | 40 | 96 | 100 |
| 0.2 | 0 | 0 | 47 | 97 |

TABLE B control of *tetranychus* sp. adults

| ABA formulation, 9 g Al/ha | Adjuvant, 17 ml product/ha | 3DAA1, % | 5DAA1, % | 7DAA1, % | 3DAA2, % | 7DAA2, % | 10DAA2, % | 15DAA2, % |
|---|---|---|---|---|---|---|---|---|
| Example K (comparative) | — | 75 | 75 | 61 | 83 | 79 | 78 | 74 |
| Example B | — | 62 | 41 | 41 | 54 | 62 | 64 | 49 |
| Example 2 | — | 79 | 55 | 56 | 67 | 79 | 68 | 58 |
| Example B | ADIGOR | 65 | 52 | 40 | 60 | 78 | 75 | 61 |
| Example B | SILWET L77 | 57 | 50 | 42 | 59 | 81 | 77 | 69 |
| Example B | ATLOX SEMKOTE E-135 | 58 | 54 | 41 | 63 | 77 | 71 | 67 |
| Example B | ATPLUS 463 | 76 | 56 | 45 | 78 | 78 | 82 | 77 |

TABLE C control of Colorado potato bettle

| ABA formulation, 9 g Al/ha | Adjuvant, 2 ml product/ha | 1DAA1, % | 3DAA1, % | 5DAA1, % | 7DAA1, % | 11DAA1, |
|---|---|---|---|---|---|---|
| Example K (comparative) | — | 100 | 97 | 74 | 66 | 35 |
| Example 2 | — | 100 | 100 | 100 | 100 | 97 |
| Example B | ADIGOR | 100 | 100 | 100 | 100 | 97 |
| Example B | SILWET L77 | 100 | 100 | 99 | 100 | 98 |
| Example B | ATLOX SEMKOTE E-135 | 100 | 100 | 100 | 100 | 98 |
| Example B | ATPLUS 463 | 100 | 100 | 97 | 100 | 97 |
| Example B | ALKAMUL BR | 100 | 100 | 100 | 100 | 97 |
| Example B | TURBOCHARGE D | 100 | 100 | 100 | 100 | 97 |
| Example B | TWEEN 80 | 100 | 100 | 98 | 100 | 95 |
| Example B | CET SPEED* | 100 | 100 | 95 | 100 | 97 |

*applied at 10.1 ml product/ha

TABLE D control of *Liriomyza Trifolii* pupae

| | 9DAA1, % |
|---|---|
| Example J (comparative) | 52 |
| Example A | 0 |
| Example 1 | 21 |
| Example B | 16 |
| Example 2 | 44 |

TABLE E recovered abamectin (ppb)

| | Abamectin (ppb) | | | | | |
|---|---|---|---|---|---|---|
| Interval (DALA) | Ex. J | Ex. A | Ex. 2 | Ex J & Dyne-Amic ® | Ex. A & Dyne-Amic ® | Ex. 2 & Dyne-Amic ® |
| 0 | 301 | 319 | 407 | 313 | 402 | 397 |
| 0.25 | 192 | 340 | 347 | 203 | 195 | 133 |
| 3 | 63 | 192 | 228 | 99 | 94 | 110 |
| 7 | 16 | 112 | 143 | 39 | 72 | 38 |
| 14 | 9 | 52 | 53 | 12 | 37 | 22 |
| 21 | 6 | 62 | 48 | 9 | 40 | 11 |

Note:
Residues reported above represent the average of two replicates expressed as Abamectin B1a (avermectin B1a and its 8,9-Z isomer) plus Abamectin B1b
No residues (<2.00 ppb) were detected in any of the controls analyzed during this study.

TABLE F recovered abamectin

| | % ABAMECTIN REMAINING - TIME AFTER IRRADIATION (Hours) | | | | | | |
|---|---|---|---|---|---|---|---|
| Treatment | 0.5 | 1 | 3 | 6 | 12 | 24 | 43 |
| Example A | | 88.2 | 49.1 | 40.5 | 30.0 | 6.5 | 1.3 |
| Example 2 | | 95.5 | 39.0 | 29.4 | 26.3 | 4.2 | 1.1 |
| Example 7 | | 93.7 | 55.2 | 29.7 | 19.6 | 4.2 | 1.7 |
| Example J (comparative) | | 91.1 | 35.0 | 25.5 | 10.3 | 8.5 | 4.4 |
| Example A + Penetrator Plus | 49.0 | 42.1 | 38.5 | 29.3 | 13.5 | 6.5 | 0.8 |
| Example 2 + Penetrator Plus | 51.0 | 38.9 | 26.4 | 15.9 | 4.0 | 0.8 | 0.0 |
| Example 7 + Penetrator Plus | 41.9 | 37.7 | 26.0 | 12.9 | 5.6 | 0.6 | 0.0 |
| Example J + Penetrator Plus | 59.5 | 41.6 | 25.3 | 19.9 | 6.5 | 1.3 | 1.2 |

TABLE G micrograms of abamectin inside the leaf tissue

| Time | Example K | Example 2 | Example 2 + oil* |
|---|---|---|---|
| 0 | 0.22 | 0.24 | 0.39 |
| 1 | 0.23 | 0.23 | 0.45 |
| 3 | 0.15 | 0.14 | 0.13 |
| 6 | 0.33 | 0.16 | 0.33 |

*oil is Horticultural spray oil, i.e. summer oil

TABLE H micrograms of abamectin on the leaf surface

| Time | Example K | Example 2 | Example 2 + oil* |
|---|---|---|---|
| 0 | 12.87 | 12.54 | 7.74 |
| 1 | 8.91 | 12.57 | 4.58 |
| 3 | 1.19 | 7.65 | 2.65 |
| 6 | 0.77 | 4.10 | 2.02 |

*oil is Horticultural spray oil, i.e. summer oil

The invention claimed is:

1. An aqueous agrochemical pesticide formulated composition in the form of a suspension concentrate or suspoemulsion comprising:
   (A) 1.5 to 15 weight % of abamectin;
   (B) 7 to 20 weight % of ethoxylated sorbitan oleate having 20 ethyleneoxy groups and a hydrophile-lipophile balance (HLB) of between 14 and 17;
   (C) one or more surfactants selected from the group consisting of ethoxylated tristyryl phenol and ethoxylated tristyrylphenol phosphate, wherein (C) is present in the formulated composition and is present in an amount up to 3 weight %;
   one or more customary formulation auxiliaries;
   water; and
   optionally (D) one or more other agrochemical pesticides different from (A);
   wherein (1) each of said weight % is based on the total weight of the formulated composition, (2) the weight ratio of (B) to (A) is from 1.6 to 10.0, and (3) (A) and (D) have a particle size in the range 0.1 to 0.9 μm at $x_{50}$ as defined in ISO 13320-1 and (A) and (D) have a particle size in the range 0.7 to 1.5 μm at $x_{95}$ as defined in ISO 13320-1.

2. The composition according to claim 1 wherein the ratio of (B) to (A) is in the range of from 1.7 to 7.0.

3. The composition according to claim 1, wherein said abamectin is present in an amount of in the range of 6 to 10 weight % and the ratio of (B) to (A) is in the range of from 1.6 to 3.0.

4. The composition according to claim 1, wherein said abamectin is present in an amount of in the range of 2 to 5 weight % and the ratio of (B) to (A) is in the range of from 4.0 to 8.0.

5. The composition according to claim 1, wherein said abamectin is present in an amount of in the range of 2 to 5, weight % and the ratio of (B) to (A) is in the range of from 4.0 to 7.0.

6. The composition according to claim 1 wherein the other agrochemical pesticide (D) is selected from the group consisting of thiamethoxam, imidacloprid, clothianidin, tefluthrin, cyflumetofen, chlorantraniliprole, cyantraniliprole, difenconazole, fipronil, azoxystrobin, and fludioxonil.

7. The composition according to claim 6 wherein the weight ratio of (D) to (A) is at least 1.5.

8. A method of improving the translaminarity of abamectin and for improving the resuspension properties of a suspension, comprising: forming the aqueous agrochemical pesticide formulated composition of claim 1.

9. A method of controlling pathogenic damage or pest damage in a plant propagation material, a plant, parts of a plant and/or plant organs that grow at a later point in time, which comprises applying on the plant, part of the plant, plant organs, plant propagation material or a surrounding area thereof the aqueous agrochemical formulated composition defined in claim 1.

10. The method according to claim 9 wherein the formulated composition is applied at a rate of 1 to 100 grams of AI per hectare.

11. A tank-mix composition suitable for directly applying on a plant, part of the plant, plant organs, plant propagation material comprising the aqueous agrochemical pesticide formulated composition of claim 1, a solvent, optionally one or more other adjuvants and optionally one or more other pesticide formulated compositions.

* * * * *